United States Patent [19]

Schucker

[11] Patent Number: 4,983,338

[45] Date of Patent: Jan. 8, 1991

[54] ISOCYANURATE CROSSLINKED POLYURETHANE MEMBRANES AND THEIR USE FOR THE SEPARATION OF AROMATICS FROM NON-AROMATICS

[75] Inventor: Robert C. Schucker, Baton Rouge, La.

[73] Assignee: Exxon Research and Engineering Company, Florham Park, N.J.

[21] Appl. No.: 496,464

[22] Filed: Mar. 20, 1990

Related U.S. Application Data

[62] Division of Ser. No. 391,058, Aug. 9, 1989, Pat. No. 4,929,357.

[51] Int. Cl.$^5$ .............................................. B01D 67/00
[52] U.S. Cl. ................................... 264/45.1; 264/298
[58] Field of Search ..................... 210/500.27, 500.28, 210/500.33, 321.61; 264/41, 45.1, 48, 556, 212, 298, DIG. 48, DIG. 62

[56] References Cited

U.S. PATENT DOCUMENTS

| 2,930,754 | 3/1960 | Stuckey | 210/23 |
| 2,958,656 | 11/1960 | Stuckey | 210/23 |
| 3,370,102 | 2/1968 | Carpenter et al. | 260/674 |
| 4,115,465 | 9/1978 | Elfert et al. | 260/674 |
| 4,359,359 | 11/1982 | Gerlach et al. | 210/321.61 |
| 4,366,062 | 12/1982 | Kurihara et al. | 210/651 |
| 4,557,949 | 12/1985 | Kurihara et al. | 427/244 |

FOREIGN PATENT DOCUMENTS

| 44872 | 2/1982 | European Pat. Off. |
| 4158379 | 12/1979 | Japan . |
| 5048205 | 4/1980 | Japan . |
| 8064102 | 4/1983 | Japan . |

Primary Examiner—Frank Sever
Attorney, Agent, or Firm—Joseph J. Allocca

[57] ABSTRACT

The present invention is directed to non-porous isocyanurate-crosslinked polyurethane membranes. These membranes are useful for the separation of aromatic hydrocarbons from non-aromatic hydrocarbons. The separation can be performed using any commonly accepted membrane separation technique, e.g. reverse osmosis, dialysis, pervaporation or perstraction but is preferably performed under pervaporation or perstraction conditions.

10 Claims, No Drawings

ISOCYANURATE CROSSLINKED POLYURETHANE MEMBRANES AND THEIR USE FOR THE SEPARATION OF AROMATICS FROM NON-AROMATICS

This is a division, of application Ser. No. 391,058, filed Aug. 9, 1989, now Pat. No. 4,929,357.

CROSS REFERENCE TO RELATED APPLICATIONS

This application is a Rule 60 Divisional of U.S. Ser. No. 391,058, filed Aug. 9, 1989.

DESCRIPTION OF THE INVENTION

Isocyanurate crosslinked polyurethane membranes, which are non-porous, have been fabricated. These membranes can be cast on a surface which does not provide a backing layer, thereby producing a symmetric membrane. Alternatively the membrane can be cast on a porous backing such as teflon, polypropylene etc. to produce an integral composite membrane. The membrane is particularly useful for separating aromatics from non-aromatics, e.g. aromatics from saturates, especially for upgrading naphtha streams. Such separations are preferably performed under pervaporation or perstraction conditions.

BACKGROUND OF THE INVENTION

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e. aromatic, unsaturated, saturated, by permeating a portion of the mixture through a non-porous cellulose ether membrane and removing permeate from the permeate side of the membrane using a sweep gas or liquid. Feeds include hydrocarbon mixtures, naphtha (including virgin naphtha, naphtha from thermal or catalytic cracking, etc.).

U.S. Pat. No. 2,930,754 teaches a method for separating hydrocarbons e.g. aromatic and/or olefins from gasoline boiling range mixtures, by the selective permeation of the aromatic through certain cellulose ester non-porous membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

U.S. Pat. No. 4,366,062 teaches reverse osmosis using a composite isocyanurate membrane. The method selectively separates at least one water soluble material from an aqueous solution. The membrane comprises microporous substrate and a barrier layer about 0.01 to 0.1 micron thick. It is composed of a crosslinked polymeric material having isocyanurate structure and substituents appended thereto selected from hydrogen, glycidyl groups and alkyl radical groups containing 2 to 5 carbon atoms which may also contain functional hydroxyl groups or glycidyl groups. The crosslinked polymeric material has ester or ether linkages or combination thereof connecting the isocyanurate structures to each other. There are no urethane groups present.

U.S. Pat. No. 4,557,949 teaches a method for making the reverse osmosis semipermeable membrane disclosed in U.S. Pat. No. 4,366,062.

European application No. 0044872 teaches selectively separating water soluble materials from a solution under reverse osmosis conditions using a membrane having a porous support layer carrying a barrier layer of crosslinked isocyanurate polymer.

Japanese Application No. 81/160960 teaches a composite membrane for reverse osmosis made by applying a solution of a barrier layer-forming component to a substrate, then heating it.

Japanese Application No. 78/121150 teaches an isocyanurate network terpolymer useful for the production of a selective permeation membrane. A polymer having hydroxyl groups and tert amine groups in the side chain is reacted with cyanuric chloride and subject to terpolymerization by reacting the tert amine groups with produced hydrochloride to give a polymerized polyisocyanurate. A polymer made using glycidyl methacrylate-styrene copolymer, diethyl amine in benzene and methanol was produced having 2-hydroxy-3-diethylaminopropyl group. This polymer was crosslinked with cyanuric chloride and cast on a PTFE plate and kept 24 hours at 40° to give a 44$\mu$ membrane. This membrane was used to separate a mixture of cyclohexane and benzene under pervaporation conditions. A permeate gas which was 100% benzene was recovered at a rate of 0.0025 g/m$^2$-hr.

DETAILED DESCRIPTION OF THE INVENTION

The present invention is directed to a non-porous isocyanurate crosslinked polyurethane membrane and its use for the separation of aromatic hydrocarbons from non-aromatic hydrocarbons e.g. aromatics from saturates as, for example, in upgrading aromatics containing streams in petroleum refineries, and chemical plants, such streams including by way of example and not limitation naphtha streams, heavy cat naphtha streams, intermediate cat naphtha streams, light aromatic streams boiling in the C$_5$-300° F. range, LCCO boiling in the 400°-650° F. range BTX containing streams, etc.

The isocyanurate crosslinked polyurethane membrane is produced employing standard membrane casting procedures. A prepolymer of polyurethane is prepared by reacting dihydroxy or polyhydroxy compounds (e.g., polyethers or polyesters) of about 250 to 5000 molecular weight, or mixtures of different molecular weight polymers of the same type with aliphatic, alkylaromatic or aromatic diisocyanates or polyisocyanates.

Mixtures of polyesters and polyethers can also be used.

This isocyanate end-capped polyurethane prepolymer is trimerized using a standard trimerization catalyst such as N,N',N''-tris(dimethylaminopropyl)-s-hexahydrotriazine, Sodium ethoxide, Potassium octoate, N-Hydroxypropyl-trimethylammonium-2-ethylhexanote, Potassium 2-ethylhexanoate, Trialkyl phosphines, 2,4,6-Tris(dimethylaminomethyl)phenol and mixtures thereof. Using these catalyst yields a mixture which slowly thickens due to crosslinking accounted for by the formation of isocyanurate crosslinked rings. Before this mixture becomes too thick, it is deposited as a thin film on an appropriate substrate and permitted to fully gel, after which the membrane coat is treated to complete the formation of isocyanurate crosslinked polyurethane. This final treat can constitute no more than waiting a sufficiently long time to be certain that trimerization is complete. More likely this final treat will involve various degrees of drying followed, preferably, by heating to complete the trimerization to the isocyanurate crosslinked polyurethane.

As previously stated, the membranes are produced by standard casting techniques from a polymer made from dihydroxy or polyhydroxy compounds, such as polyethers or polyester of 250 to 5000 molecular weight, end capped with aliphatic, alkylaromatic or aromatic diisocyanates or polyisocyanates to form a polyurethane prepolymer which is then trimerized through the free isocyanate group using a catalyst to produce the isocyanurate crosslinked polyurethane. The end capped polyurethane prepolymer is produced using a 1:2 mole ratio of diol with diisocyanate.

The polyester polyol components are prepared from aliphatic or aromatic dicarboxylic acids and aliphatic or aromatic dialcohols. Aliphatic dicarboxylic acids refer to those materials having the general formula HOOCR-COOH where R contains 2 to 10 carbons (and may be either a straight or branched chain configuration). Aromatic dicarboxylic acids refer to those materials having the general structure HOOCRCOOH where R is:

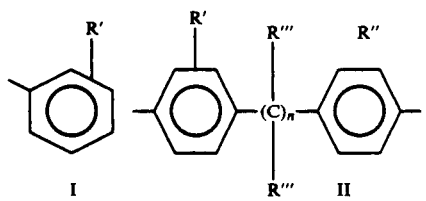

wherein R', R" and R'" may be the same or different and are selected from the group consisting of H and $C_1$-$C_5$ carbons or $C_6H_5$ and combinations thereof, and n is 0 to 4. It is to be understood that in the above formula each R' or R" may itself represent a mixture of H, $C_1$-$C_5$ or $C_6H_5$.

Dialcohols have the general structure HOROH where R may be

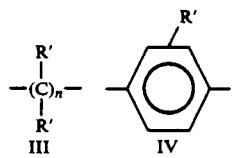

where n is 1 to 10, preferably 4 to 6, and R, is H, $C_1$ to $C_5$ or $C_6H_5$ or

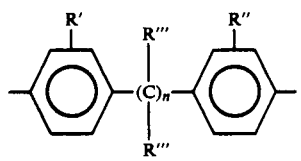

where R', R", R'" and n are defined in the same for the aromatic dicarboxylic acids. An example of a useful dialcohol is bisphenol A.

The diisocyanates are preferably aromatic diisocyanates having the general structure:

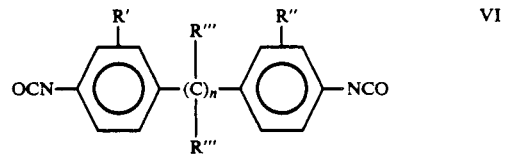

wherein R' and R" are the same or different and are selected from the group consisting of H, $C_1$-$C_5$ and $C_6H_5$ and mixtures thereof and n ranges from 0 to 4.

Examples of the polyether polyols useful in the present invention as polymer precursors are polyethylene glycol, (PEG), polypropylene glycol (PPG), polytramethylene glycol, PEG/PPG random copolymers, etc. having molecular weight ranging from about 250 to 4000. Aliphatic diisocyanates which may be utilized are exemplified by hexamethylene diisocyanate (HDI), 1,6-diisocyanato-2,2,4,4-tetramethylhexane (TMDI), 1,4-cyclohexanyl diisocyanate (CHDI), isophorone diisocyanate (IPDI), while useful alkylaromatic diisocyanates are exemplified by toluene diisocyanate (TDI) and bitolylene diisocyanate (TODI). Aromatic diisocyanates are exemplified by 4,4'-diisocyanato diphenylmethane (MDI). Polyisocyanates are exemplified by polymeric MDI (PMDI) and carbodiimide modified MDI.

Trimerization catalysts are exemplified by N,N',N"-tris(dimethylaminopropyl)-s-hexahydrotriazine, Sodium ethoxide, Potassium octoate, N-Hydroxypropyl-trimethylammonium-2-ethylhexanote, Potassium 2-ethylhexanoate, Trialkyl phosphines, and mixtures thereof.

The above are presented solely by way of example. Those skilled in the art, with the present teaching before them, can select from the innumerable materials available the various starting materials which upon combination as described herein will produce a polyisocyanate crosslinked polyurethane which can then be cast into the membranes useful for the separation of aromatics from saturates.

The membranes are produced by preparing the polyisocyanurate crosslinked polyurethane in an appropriate solvent, such as Dimethylformamide (DMF), N-methyl pyrrolidone (NMP), 2-Ethoxyethyl acetate (cellosolve acetate), Dimethyl acetamide (DMAC), Dimethyl sulfoxide (DMSO) and mixtures thereof, to produce a pourable, spreadable solution. To this end, once the components are mixed, the mixture should be poured or spread before the isocyanurate polymer gels to too high a viscosity. Thus, the isocyanurate crosslinking polyurethane mixture can be poured or spread almost immediately upon the addition of the trimerizing catalyst, if the surface on which it is poured or spread is not porous. A thin film of this mixture is left on the surface (glass, metal, non-porous fabric etc.) and permitted to trimerize over time until the reaction to the isocyanurate-crosslinked polyurethane is completed. Alternatively if a porous support is used, in order to prevent the casting solution from simply soaking through the surface or becoming embedded in the pores of the fabric or backing, the casting mixture is left to stand so as to gel to some extent prior to being poured or cast onto the support.

In either case, after the casting solution has been spread and has gelled it can be left to complete its trimerization simply by standing. Alternatively the gelled film can be dried in air or inert gas stream at 25°–100° C. to induce completion of crosslinking. Preferably following drying the film may be heated if necessary at 50°–100° C. in air or other gas or vacuum to complete trimerization to the polyisocyanurate.

The casting solution of end capped polyurethane and catalyst in solvent has a concentration of 1 to 50 wt % polymerization component in solvent, preferably 2 to 25 total wt % components in the solvent.

In general the backing or support can be glass, metal, woven fabric, or non-woven fabric. Woven fabric backing includes woven fiber glass, nylon, polyester etc. Non-woven backings include non-woven porous polypropylene or teflon. The backing is one which is not attacked by the solvent used to produce the casting solution. It is also one which will stand up to the environment to which the active membrane layer will be exposed. That environment includes the materials in the mixtures to be separated as well as the temperatures used in the separation. Clearly, separations practiced at elevated temperatures require the use of a high temperature backing, e.g. sintered metal or teflon rather than polypropylene.

The membrane active layer (i.e. membrane less any backing or support which may be used) may be cast in any thickness, membranes ranging in thickness of from about 0.1 to about 50 microns being preferred.

Alternatively a very thin layer of the casting solution (gelled to a manageable viscosity) can be deposited into a highly permeable, non-porous, non-selective polyurethane layer producing a composite membrane comprising a thin, dense, selective layer of isocyanurate-crosslinked polyurethane which would otherwise be mechanically unmanageable due to their thinness. Due to the chemical similarity between the polyurethane support layer and the isocyanurate-crosslinked polyurethane active, selective layer, the two layers interact through hydrogen bonding to produce a very strong adhesion.

If one were to use this technique to produce sheet material, the thick, permeable polyurethane layer can be deposited on a suitable backing material such as porous fiber glass, polyethylene, polypropylene, nylon, teflon, etc. after which the thin, dense selective polyurea/urethane layer would be deposited onto the polyurethane layer.

In producing hollow fibers or tubes using this composite membrane technique, first a tube or hollow fiber of suitable support material, such as nylon, teflon or permeable polyurethane is produced after which a thin dense layer of the selective polyisocyanurate crosslinked polyurethane material is deposited on either the outer or inner surface of the tube or fiber support. It is also possible to deposit a layer of the aforesaid porous polyurethane on the hollow fiber and then put down a thin, dense film of polyisocyanurate crosslinked polyurethane thereon.

The permeable polyurethane layer can be prepared from polyether glycols such as polypropylene glycol or polybutylene glycol plus aliphatic and/or aromatic diisocyanates (preferably aliphatic diisocyanates) using polyols (diols or triols) preferably aliphatic diols as chain extenders. These permeable polyurethane sublayers will possess characteristics well outside the minimums recited for the polyurea/urethane membranes taught herein. Polyurethane membrane materials which satisfy the above requirement of permeability are the polyurethane membranes described in U.S. Pat. No. 4,115,465.

The membranes are useful for the separation of aromatics from saturates in petroleum and chemical streams, and have been found to be particularly useful for the separation of large substituted aromatics from saturates as are encountered in heavy cat naphtha streams. Other streams which are also suitable feed streams for aromatics from saturates separation are intermediate cat naphtha streams, (200°–320° F.) light aromatics content streams boiling in the $C_5$–300° F. range, light catalytic cycle oil boiling in the 400°–650° F. range as well as streams in chemical plants which contain recoverable quantities of benzene, toluene, xylene (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into an migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and re-emerge on the permeate side under the influence of a concentration gradient. Pervaporative separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher should be used, the maximum upper limit being that temperature at which the membrane is physically damaged. Vacuum on the order of 1–50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

Most conveniently, the membrane is used in a hollow fiber configuration with the feed introduced on the exterior side of the fiber, the sweep liquid or vacuum being on the inside or outside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

The present invention will be better understood by reference to the following Examples which are offered by way of illustration and not limitation.

EXAMPLE 1

Twenty-five point two nine grams (approximately 0.05 mole) polyethylene adipate (500 MW) and 25.0 grams (0.10 mole) methylene diisocyanate were placed in a wide mouth round bottom flask equipped with a mechanical stirrer. The mixture was stirred and heated at 95° C. for 2 hours to form an isocyanate-capped urethane prepolymer. One gram of this prepolymer was dissolved in 17 grams of DMF to which was added 2 grams of DMF containing 0.01 gram 2,4,6-Tris(dimethylaminomethyl)phenol (DABCO TMR-30) and 0.002 gram Potassium 2-ethylhexanoate (DABCO K-15) catalysts. The solution was stirred until it began to thicken due to crosslinking reactions (approximately 60 minutes); and then a small amount of it was poured onto a piece of porous Teflon membrane (DSI K-100, 0.02μ pore size). The crosslinking continued until the layer on the Teflon had completely gelled up. The coated Teflon was air dried for 30 minutes, then placed into an oven at 160° C. overnight under a constant nitrogen purge to complete the formation of the polyisocyanurate. It was tested for perstractive separation of saturates from aromatics in a small laboratory membrane testing unit at 86° C. using n-heptane as the sweep liquid and a feed consisting of 14.6 wt % p-xylene, 28.1 wt % mesitylene, 13.0 wt % 1-decene and 44.3 wt % n-decane. The run was subsequently repeated at 113° C. using n-hexadecane as the sweep. Results from both runs are shown in Table 1 below.

TABLE 1

| Perstraction of Model Feed with a Isocyanurate-Crosslinked Polyurethane Membrane | | |
|---|---|---|
| Temperature (°C.) | 86 | 113 |
| Flux (kg/m²/d) | 0.101 | 0.416 |
| Selectivity (vs n-decane) to | | |
| p-xylene | 16.75 | 15.83 |
| mesitylene | 7.66 | 7.18 |

As can be seen from the data, the selectivity of these membranes to aromatics is quite good. In addition, because this is a crosslinked polymer, the selectivity does not show much decline with elevated temperature while the flux increased fourfold. The relatively low absolute flux rates can be increased by making the membranes thinner.

What is claimed is:

1. A method comprising producing a non-porous isocyanurate crosslinked polyurethane membrane having properties at least sufficient for enabling the separation from mixture of the same with non-aromatic Hydrocarbons, by, preparing a prepolymer of polyurethane by reacting dihydroxy or polyhydroxy compounds with a di or poly isocyanate, trimerizing this prepolymer using a trimerization catalyst to produce a casting solution mixture which slowly thickens due to cross-linking caused by the formation of isocyanurate cross-linked rings, depositing this casting solution on a substrate to produce a thin film, permitting the thin film to fully gel into the desired isocyanurate cross-linked polyurethane membrane.

2. The method of claim 1 wherein the thin layer of casting solution is dried to produce the desired isocyanurate crosslinked polyurethane membrane.

3. The method of claim 1 wherein the layer of casting solution is heated to complete trimerization to produce the desired isocyanurate crosslinked polyurethane membrane.

4. The method of claim 1, 2 or 3 wherein the dihydroxy or polyhydroxy compound and the di or poly isocyanate compound is used in a mole ratio of 1:2.

5. The method of claim 1, 2 or 3 wherein the casting solution is prepared by mixing the components in the presence of a solvent.

6. The method of claim 5 wherein the solvent is selected from dimethylformamide (DMF), N-methyl-pyrrolidone (NMP), 2-ethoxyethyl acetate (cellosolve acetate), dimethylacetamide (DMAC), dimethyl sulfoxide (DMSO) and mixtures thereof.

7. The method of claim 5 wherein the casting solution has a concentration of 1 to 50 wt % polymerization component in solvent.

8. The method of claim 1, 2 or 3 wherein the casting solution is spread on a substrate selected from nonwoven polypropylene or teflon.

9. The method of claim 1, 2 or 3 wherein the casting solution is spread on a substrate comprising highly permeable, non-porous, non-selective polyurethane layer.

10. The method of claim 1, 2 or 3 wherein the casting solution is spread on either the inside or outside surface of a hollow fiber of suitable support material.

* * * * *